United States Patent [19]

Bude et al.

[11] Patent Number: 4,755,618

[45] Date of Patent: Jul. 5, 1988

[54] RECOVERY OF ACTIVE TANNIN FROM SCHOENE SLUDGE

[75] Inventors: Duane A. Bude, St. Louis County; Ellen Y. Lin, Chesterfield, both of Mo.

[73] Assignee: Anheuser-Busch, Incorporated, St. Louis, Mo.

[21] Appl. No.: 57,352

[22] Filed: Jun. 2, 1987

Related U.S. Application Data

[63] Continuation-in-part of Ser. No. 866,228, May 22, 1986, abandoned.

[51] Int. Cl.$^4$ .............................................. C07C 69/88
[52] U.S. Cl. ......................................... 560/68; 560/69
[58] Field of Search .................................... 560/68, 69

[56] References Cited

U.S. PATENT DOCUMENTS 2,214,251  9/1940  Lewis ................................. 560/68 X
2,694,725  11/1954  Filachione et al. .................... 560/68

Primary Examiner—Werren B. Lone
Assistant Examiner—Vera C. Clarke
Attorney, Agent, or Firm—Gravely, Lieder & Woodruff

[57] ABSTRACT

A process for recovering active gallotannin for reuse comprising the extracting of dried schoene sludge (about 5% moisture) with a mixture of about 88 vol. % acetone—12 vol. % water to solubilize the gallotannins. The solvent is evaporated off, the residue is treated with water to solublize the gallotannins. After filtration, the clarified water solution is extracted with ethyl acetate. Evaporation of ethyl acetate leaves purified gallotannin which can be redissolved in water and spray dried to produce reusable powder. A preliminary step of separating yeast from the gallotannin protein complex involves treating with 60% acetone/40% $H_2O$ at room temperature before making the solution about 88:12 acetone:water.

22 Claims, 1 Drawing Sheet

RECOVERY OF ACTIVE TANNIN FROM SCHOENE SLUDGE

RELATED APPLICATION

This application is a continuation-in-part of pending application Ser. No. 866,228 of Duane A. Bude and Ellen Y. Lin filed May 22, 1986 entitled RECOVERY OF ACTIVE TANNIN FROM SCHOENE SLUDGE, now abandoned.

BACKGROUND OF THE INVENTION

This invention relates to the recovery of active tannin from schoene sludge in a beer production plant whereby the tannin can be reused in making beer.

In order to be commercially acceptable, a beer must possess certain properties; for example, it must be sparkling clear. An additional property which is most significant to beer connoisseurs is referred to as chill stability. This relates to the property noted above as "sparkling clear". As the name "chill haze" implies, a haze usually forms in beer when it is chilled. As the temperature of the beer is returned to room temperature, the haze usually disappears, only to reappear upon subsequent re-chilling.

Several methods are used in the brewing industry for chillproofing of beer, the method of choice depending on the process economics and on the flavor characteristics desired in the end product.

One of the methods widely used in the trade for chillproofing of beer is based on the precipitation and removal of proteinaceous constituents from beer using a solution of tannic acid derived from plants. Other methods of precipitation include bentonite and silica gel addition.

This invention relates to the chillproofing process using tannic acid. One of the ways tannic acid (tannin) is added to the beer from a lager tank as it enters a schoene or chillproofing tank. In the schoene tank, the tannin reacts with proteins to form what is called a "schoene sludge" which precipitates out. The clear beer is decanted off and undergoes further clarification. The sludge is the material which is the subject of this invention.

"Tannin" is a generic term for substances able to form complexes with proteins and protein-like substances. Most tannins are some type of polyphenol, but not all polyphenols are tannins. Presently, commercial tannins are purchased from manufacturers and are used in the beer chillproofing process. These commercial tannins are of the hydrolyzable gallotannin type and are homologous mixtures of many gallotannins. Most of the gallotannins presently used in chillproofing are composed of two compounds, glucose and gallic acid.

Many different arrangements and ratios of gallic acid:glucose are present in gallotannins. The different ratios produce different molecular sizes and different arrangements produce isomers which are compounds of the same empirical formula but different structural arrangement.

Commercial tannins presently are made from gallnuts and sumac leaves. The tannins are extracted from natural sources with methyl isobutyl ketone and water or acetone and water, purified and spray dried.

When the tannin is added to the beer in the schoene process, it bonds to some of the proteins, peptides and carbohydrates in the beer to form what is called "schoene sludge". Yeast is also co-precipitated. The bonding is strong and is believed to be of three types: hydrogen bonding between phenolic and protein ketoimide groups; hydrophobic interactions between the aromatic ring structures and the hydrophobic regions of proteins; and ionic bonding between the phenolate anion and the cationic site of the protein molecule.

Traditionally the sludge is discarded. However, present day environmental regulations make this costly. Also, the tannin is expensive and it would be advantageous to reuse it. Furthermore, the residue from the sludge separation is more acceptable as animal feed if the tannins are removed as animals cannot digest tannin material properly.

Accordingly it is a principal object of this invention to provide a process for recovering chillproofing active tannin from schoene sludge produced in a beer making process. It is important that the tannin retain its chillproofing properties as it is possible to recover tannin which is not active. Inactive material has no value in chillproofing of beer.

These and other objects and advantages will become apparent hereinafter.

SUMMARY OF THE INVENTION

This invention concerns the recovery of active gallotannins from schoene sludge by treating the sludge with a mixture of acetone and water in the ratio of 85 to 95% acetone to 15 to 5% water, preferably 88% acetone to 12% water.

The invention also consists in the parts and compositions and in the arrangements and combinations of parts and compositions hereinafter described and claimed.

THE FIGURE

The FIGURE is a chromatographic comparison of commercial tannin and tannin recovered by the process of this invention. FIG. 1A is a chromatograph of commercial tannin and FIG. 1B is a chromatograph of tannin extracted from Schoene sludge by the process of this invention. The HPLC chromatographic conditions are $7.8 \times 300$ mm Waters $C_{18}$ column, 100 to 65% water ($H_3PO_4$)/35% acetonitrile, gradient #0.2, 70 minute gradient, 2.5 ml/min., $UV^{254}$.

DETAILED DESCRIPTION

A typical sludge from a schoene tank has approximately the composition shown in Table No. 1.

TABLE NO. 1

| COMPOSITION OF A TYPICAL SLUDGE SAMPLE | |
|---|---|
| | % By Weight |
| Gallotannin | 5% |
| Carbohydrates | 70% |
| Protein-like material | 20% |
| METALS | PPM |
| Chromium | 0.07 |
| Zinc | 0.13 |
| Cadmium | 0.002 |
| Lead | 0.002 |
| Arsenic | 0.06 |
| Aluminum | 0.08 |
| Iron | 0.14 |
| Silicon | 24 |
| Manganese | 0.13 |
| Magnesium | 65 |
| Calcium | 32 |
| Copper | 0.19 |
| Sodium | 30 |

TABLE NO. 1-continued

| COMPOSITION OF A TYPICAL SLUDGE SAMPLE | |
| --- | --- |
| Potassium | 376 |

In preparing the schoene sludge for extraction to remove and recover the gallotannins for reuse, the following procedure is used:

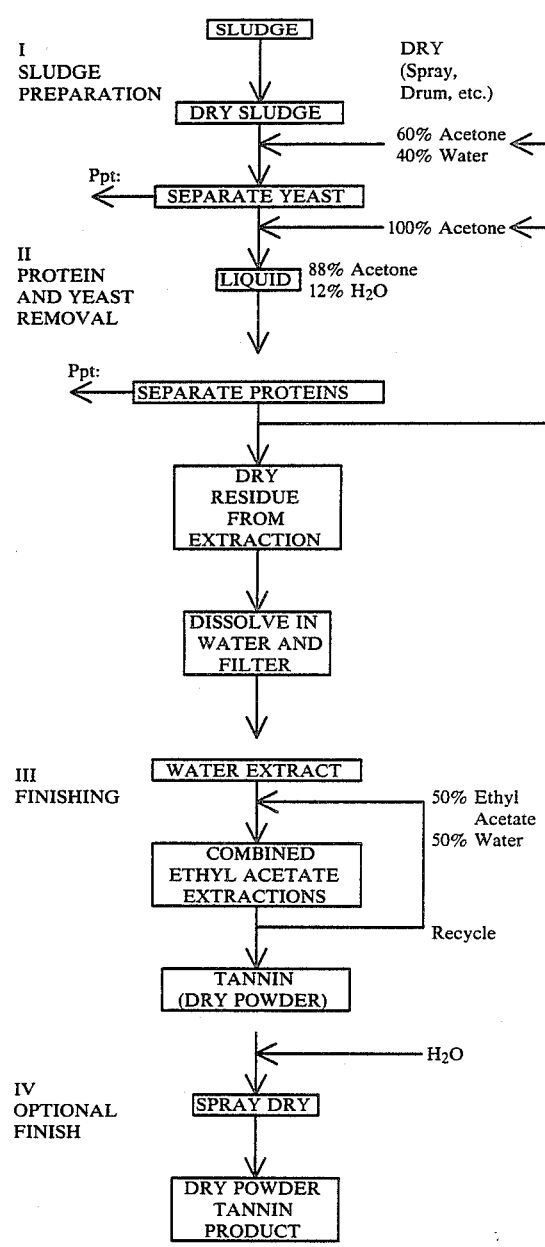

This process is described in detail under the heading Preferred Process Using Dried Sludge, and allows the separation and recovery to be done at room temperature.

Following is an alternative procedure described in the heading Alternative Process Using Dried Sludge and in this process the initial treatment with 88:12 acetone to water mix is at about 60° C. to avoid a clumping problem and allows a standard mixer to be used.

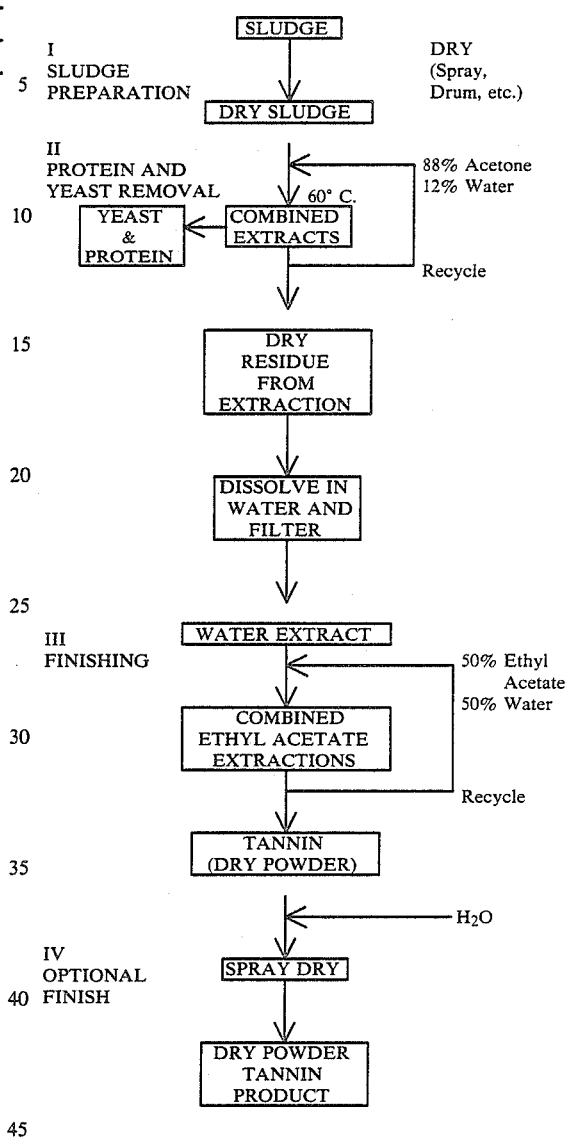

As will be described hereinafter, it is critical to the yield that the ratio of acetone to water be from about 85-15 to about 95-5 and the ratio preferably is 88% acetone and 12% water. Thus, the schoene sludge preferably is dried to less than 5% water so the amount of water in the extraction process can be carefully controlled without the use of large amounts of acetone.

Figure 1A:
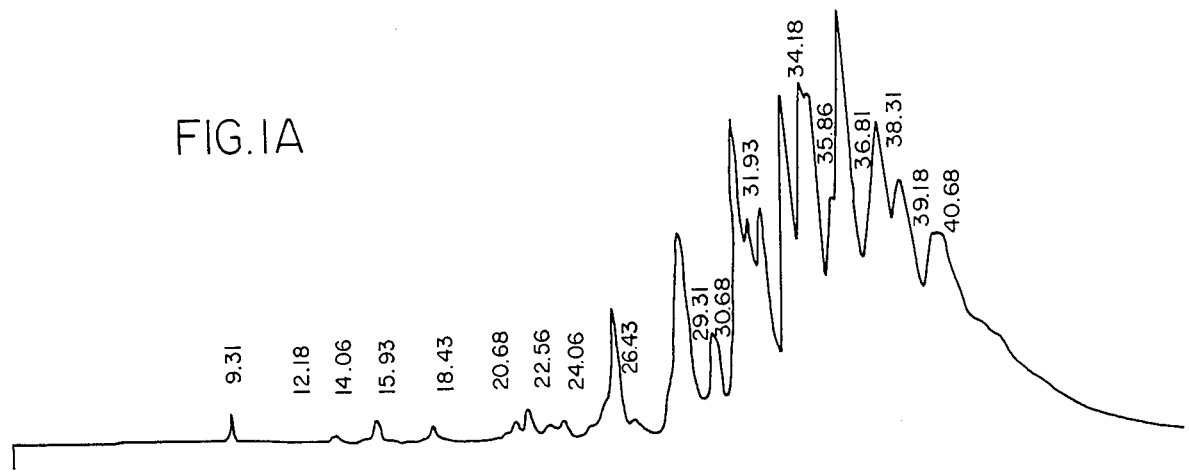
Figure 1B:
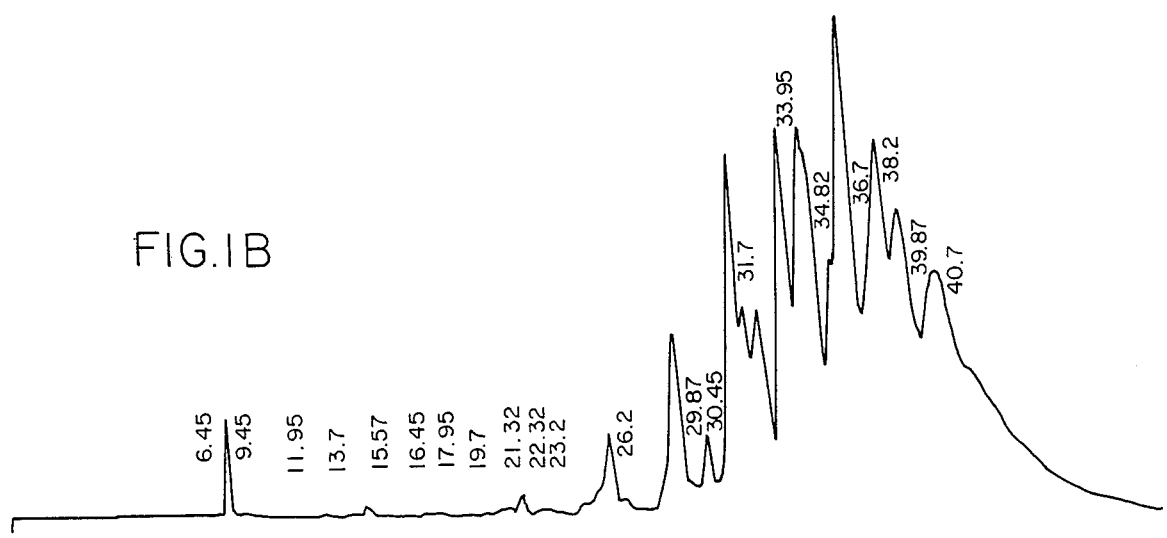

We have found that the overall extracting solvent polarity is of prime importance in separating complexed nongallotannin components from gallotannin complex found in schoene sludge. It is more important to gallotannin yield from schoene sludge than it is to extraction from natural materials, i.e. plant raw materials. Gallotannin can be extracted from plant material in ranges of 50% acetone—50% water to 100% acetone, as well as with other organic solvents, e.g. alcohol, methyl isobutyl ketone, etc. In the natural plants, the gallotannins are not complexed with the same type compounds as in schoene sludge. This optimum polarity is best achieved by a combination of acetone and water. When the overall polarity is greater than that produced by approximately 88% acetone/12% water mixture, i.e., when the water content of the mix is greater than about 15% water, then increasing amounts of inactive gallotannin complex is co-dissolved with freed active gallotannin. When the overall polarity is less than that produced by an 88% acetone/12% water mixture, i.e., when the mix contains substantially less than about 12% water, then not all of the freed active gallotannin is dissolved. Therefore, we prefer that the starting schoene sludge be dried to less than five weight percent water before extraction, so that the overall solvent polarity can be accurately controlled. The gallotannin material obtained from schoene sludge by this process is nearly identical to the original material (as shown by the chromatographic comparison of FIG. 1) and is as active in chillproofing as the original material. Therefore, gallotannin can be recycled since it will not bind with any more non-gallotannin components in later cycles than it did in the first cycle.

The starting materials can be in any of four different forms and will still produce active gallotannins when extracted with a final acetone/water mixture of approximately 88% acetone/12% water. These include: sludge spray dried at nearly atmospheric pressure; drum dried, etc. to about 5% moisture; concentrated wet sludge from decantation; wet sludge cake produced by centrifuging wet sludge; and air dried sludge. If the amount of water in these materials is substantially in excess of 5%, the amount of acetone added must be such as to produce a final extraction concentration of approximately 88% acetone/12% water. The more acetone required, however, the less desirable the process becomes in an economic sense.

As noted, all of these materials are first reduced to about 5% water by drying or by adding sufficient anhydrous acetone to produce 5% water. When the starting material is at about 5% water, it is extracted with an acetone/water mixture such that the total amount of water in the mix is about 12% and the total amount of acetone is about 88%. The extraction is repeated and the acetone is evaporated off and recycled.

The dried residue is dissolved in a small amount of water and filtered to remove undissolved material. The clarified aqueous solution is extracted twice with equal volumes of ethyl acetate and each ethyl acetate extract removed. The combined ethyl acetate extractions contain the dissolved gallotannin. The ethyl acetate is removed and recycled. The dried residue is purified recovered tannin.

To commercially finish the product and produce a dry yellowish tannin powder comparable to unused tannin as it comes from the manufacturer, the recovered tannin from the ethyl acetate extractions is dissolved in water and spray dried.

Separation of gallotannin molecules from bound nitrogenous substances requires the simultaneous breaking of all effective bonds between the phenolic groups and the active sites on the protein surface, which on a probability basis can be considered rare, diminishing in frequency as the number of linkages per bound molecule increases.

Introduction of polar organic solvent molecules into the aqueous environment permits the random transfer of individual bonds within the protein to competing sites of the solvent at rates dependent on the concentration and on the strength of the tannin-solvent interaction. The role of aqueous organic solvents appears to be attributable to the effective "blocking" of the reactive hydrogen bonding sites on the tannin by the shielding effect of local hydrophobic structure and the degree of polarity in the organic solvent used. The amount of water used in the organic solvent is used to "fine tune" the total polarity of the solvent to a polarity necessary to achieve complete separation of the tannin from the protein.

An appropriate solvent polarity can be obtained at an aqueous acetone ratio very close to 88% acetone/12% water. When the overall polarity is significantly higher due to the presence of more water, then relatively large amounts of bound nitrogenous material are dissolved along with the gallotannin producing inactive material. When the overall polarity is significantly lower due to the presence of less water, then very little gallotannin or gallotannin complex dissolves. Therefore, there is an optimum composition range that will first separate and then dissolve gallotannin but not dissolve the separated nitrogenous and carbohydrate components. These nitrogenous and carbohydrate components are soluble in acetone or ethanol when significant amounts of water are present and this is what makes separation of gallotannin from the complex derived from schoene sludge difficult. If gallotannin were complexed only with a substance that itself could not be solubilized, e.g., collagen in leather, then separation of bound gallotannin would not be as sensitive to overall solvent polarity.

Following are three different but related processes, all of which use the critical acetone:water ratio of about 88:12 to separate the active tannins from the complex. The processes differ in temperature and some pretreatment steps to separate various of the impurities out of the mix.

PREFERRED PROCESS USING DRIED SLUDGE

1. Schoene sludge from a settling tank is centrifuged, filtered, or decanted, to remove some of the water (beer).
2. The concentrated sludge is dried further, e.g., by spray (low pressure), drum or fluidized bed drying to about 5% moisture. High pressure spray drying is undesirable because it produces an irreversible reaction making it impossible to extract the gallotannins.
3. For every gram of dried sludge, 1½ ml of approximately 60% acetone/40% water (v/v) is added at room temperature. The slurry is stirred for at least about 15 minutes to solubilize the gallotannin complex from the other solids. The ratio of acetone:water can vary from about 50:50 to 70:30. Using the aforesaid acetone/water ratio allows the separation to be done at room temperature without the formation of tacky, solid lumps.
4. The brown liquid containing the gallotannin complex is separated from the insoluble material (mainly yeast) by settling and decantation, filtration, or centrifugation.
5. At this point 100% acetone is added to the liquid until the ratio of acetone:water is about 88:12 (v/v). This breaks the protein-tannin complex and causes the tannin to remain in solution with the remaining proteins precipitating out in the form of tacky solids. The range of acetone:water can vary from about 85:15 to about 95:5.
6. The liquid is decanted off and filtered with cellulose pulp filter aid to produce a clear amber solution of dissolved tannin.
7. The aqueous acetone is removed via a solvent recovery system.
8. The solvent mixture is recycled to steps 3 and 5.

9. Water is added to the residue, agitated, and filtered to remove water insolubles, e.g., remaining complexed gallotannin and lipids.
10. The clarified aqueous solution is extracted twice with equal volumes of ethyl acetate, separated and the ethyl acetate extracts are combined.
11. The ethyl acetate is removed via a solvent recovery system.
12. The ethyl acetate is recycled in step 10.
13. The residue is dissolved in a minimum amount of water and spray dried to give a reusable tannin product in powder form.

ALTERNATIVE PREFERRED PROCESS

1–3. Same.
4–5. Without decanting or otherwise separating the yeast solids, enough 100% acetone is added to the solution from step 3 to make an 88% acetone/12% water solution. The ratio of acetone/water can vary from about 85:15 to about 95:5. The tannin stays in solution and the complexed protein precipitates out, joining the previously participated out insoluble yeast, etc. to form a large tacky mass.
6–13. Same.

ALTERNATIVE PROCESS USING DRIED SLUDGE

1. Schoene sludge from a settling tank is centrifuged, filtered, or decanted, to remove some of the water (beer).
2. The concentrated sludge is dried further, e.g., by spray (low pressure), drum or fluidized bed drying to about 5% moisture. High pressure spray drying is undesirable because it produces an irreversible reaction making it impossible to extract the gallotannins.
3. For every gram of dried sludge, 3 ml of 88 vol. % aqueous acetone is added and extracted with some agitation for 2–4 hours at about 60° C. in a closed container. It is necessary to use the higher temperature to avoid forming a thick clump of material which is difficult to process and agitate.
4. Agitation is stopped, the mix is allowed to settle briefly, decanted and the acetone extract is saved.
5. The extraction of step 3 is repeated two more times with 2 ml solvent/gram sludge and the three extracts are combined.
6. The aqueous acetone is removed via a solvent recovery system.
7. The solvent mixture is recycled to steps 3 and 5.
8. Water is added to the residue, agitated, and filtered to remove water insolubles, e.g., remaining complexed gallotannin and lipids.
9. The clarified aqueous solution is extracted twice with equal volumes of ethyl acetate, separated and the ethyl acetate extracts are combined.
10. The ethyl acetate is removed via a solvent recovery system.
11. The ethyl acetate is recycled to step 9.
12. The residue is dissolved in a minimum amount of water and spray dried to give a reusable tannin product in powder form.

In addition to extracting active gallotannins with the 88% acetone/12% water mixture, we have tried to separate active gallotannins from sludge using methyl isobutyl ketone (MIBK), methanol, ethanol, butanol, enzymes, and other techniques. In the following Tables are results of this work. These data are obtained using the indicated reagents and equipment and experimental procedures.

EXPERIMENTAL PROCEDURES

Quick Test for Chillproofing Activity

Commercial gallotannin preparations are completely soluble in 0.2 M pH 4.6 phosphate buffer. However, gallotannin complexes isolated from schoene sludge or precipitate produced by addition of commercial tannin to chip beer produces copious precipitate. Both commercial tannins and isolated gallotannin complex cause precipitates to form when added to clarified chip beer.

Therefore, a test solution that causes a precipitate in both pH 4.6 buffer and chip beer contains at least some inactive material. This is because gallotannin complexed with nitrogenous material is insoluble at this pH and ionic strength. A precipitate in the chip beer, but little or none in the buffer, indicates nitrogen-free gallotannin.

Pilot Plant Tests

Recovered tannin is tested on a small scale in non-chillproofed plant beer and is found to be taste acceptable and chill-haze free.

Characterization of Isolates a. HPLC

Chromatograms are run on all isolates to qualitatively estimate if (1) degradation has occurred to give lower molecular weight gallotannins, and to (2) give an approximation of the amount of non-gallotannins present.

b. Gallotannin Assay

This standard procedure is used to measure the amount of gallotannin in both the isolates and the residues from the isolated material.

Extraction Techniques

Schoene sludge is obtained in concentrated form from a plant settling tank. This material is used as the starting point in extraction experiments. For many experiments, the sludge is slurried up in water and the pH adjusted to 8.5 with concentrated NaOH. HPLC shows that the gallotannin complex can be solubilized by this treatment. Centrifugation then separates the dissolved complex from other insoluble materials. The dark brown solution is then treated with concentrated $H_3PO_4$ causing a copious amount of cream-colored precipitate to form. Centrifugation of this mixture produces a solid complex, free of many non-complexed materials. This material is referred to as "acid-precipitated complex" in subsequent discussions.

Whole schoene sludge is dried to a low (1.7 weight percent) moisture content by passing air over sludge which previously had been concentrated by centrifugation. It dries to a brown, granular material that flows readily. When the sludge is heated to drive off the moisture, it forms a hard solid mass which needed to be broken up before extraction.

A. Alcohol Extractions

1. Ethanol

Aqueous ethanol is tested at 50, 60, 70, 80, 90, and 95 volume % (ethanol/water) for extraction of undried and air-dried acid-precipitated complexes. Each extraction is performed two times with approximately 2:1 solvent to solids ratio. The extracts in each experiment are combined and analyzed for extracted gallotannin by HPLC and activity by the quick test.

2. n-Propanol

Aqueous propanol is tested as above at 70 and 90 volume percent aqueous propanol for extraction of non-dried acid-precipitated complex. The extracts are combined for each experiment and analyzed for gallotannin and activity by the quick test.

3. n-Butanol

Butanol is saturated with water and the undried acid-precipitated complex is extracted three times with approximately 2:1 solvent to solids ratio. Similarly, the complex is also extracted with 67% butanol/33% water (2-phase). Both extracting solvent phases are analyzed for gallotannin by HPLC and tested for activity by the quick test.

TABLE NO. 2

EXTRACTION OF SCHOENE SLUDGE WITH ALCOHOLS

| Alcohols | % H$_2$O | Gallotannin Extracted (HPLC) | Activity (Quick Test) |
|---|---|---|---|
| Methanol | 30 | Moderate | Very Poor |
| Methanol | 10 | Moderate | Very Poor |
| Ethanol | 50 | Moderate | Very Poor |
| Ethanol | 40 | Moderate | Very Poor |
| Ethanol | 30 | Good | Poor |
| Ethanol | 20 | Good | Poor |
| Ethanol | 10 | Good | Poor |
| Ethanol | 5 | Good | Poor |
| n-Butanol | Saturated | Very Little | Very Little |
| n-Butanol | 33% as 2-Phase | Very Little | Very Little |

B. Displacement Reactions

1. PVPP

Acid-precipitated complex (25 grams, wet weight) is slurried in 100 ml of water and the pH adjusted to 8.5 with NaOH to dissolve the complex. Polyvinypolypyrrlidone (PVPP, 25 grams) is added and the mixture stirred at room temperature overnight. The PVPP is recovered by centrifugation and the centrate analyzed for losses in solubilized complex.

The PVPP is then extracted twice with 100 ml of aqueous 95% ethanol and the extracts combined and analyzed by HPLC for gallotannin and the quick test for activity. One hundred ml of water is then added to the PVPP, the pH adjusted to 10, the slurry centrifuged and the centrate decanted off the PVPP. The solution is immediately checked for gallotannin and activity by the quick test.

2. XAD-2

Amberlite XAD-2, a divinylbenzene crosslinked polystyrene (25 grams) is slurried up in solubilized complex at pH 8.5. After 24 hours the mixture is centrifuged and the solution analyzed for reduction in complex in solution. The XAD-2 is extracted with aqueous 90% ethanol (100 ml) and the ethanol examined for gallotannin and activity. The XAD-2 is then extracted with 100 ml 90% acetone and analyzed for gallotannin and activity by the quick test.

3. Preparative HPLC

Five grams of acid-precipitated complex are solubilized in 10 ml of 95% aqueous ethanol. The HPLC is set up using a 7.8×300 Waters semi-preparative C$_{18}$ column equilibrated with 100% water, pH 3 (H$_3$PO$_4$) at 2.5 ml/min. Two ml of the complex solution is injected and, after five minutes, the HPLC solvent is changed to 85% acetone/15% water, 2.5 ml/min. The column is eluted and the eluent collected until the detector returned to near the original baseline. The column is washed with 60% ethanol/40% water to remove non-acetone soluble proteinaceous material. The acetone and water are removed from the collected material by evaporation, and the residue extracted with water and analyzed for gallotannin by HPLC (original chromatographic conditions) and for activity by the quick test.

4. Ultrafiltration

One hundred ml of undried acid-precipitated complex is slurried up in 300 ml of water and the pH adjusted to 8.5 with NaOH. The solution is passed through an Amicon hollow fiber concentrator CH4 with an H1P10-8, MW cut-off 20,000 hollow fiber cartridge. The dark solution that comes through the cartridge is analyzed by HPLC for gallotannin and the quick test for activity by the quick test.

A similar experiment is performed using an H1P2-43, MW cut-off 2,000 cartridge. The clear solutions that come through the cartridge are analyzed for gallotannin and activity by the quick test.

TABLE NO. 3

MISCELLANEOUS EXTRACTION TECHNIQUES OF SCHOENE SLUDGE

| Type | Special Conditions | Gallotannin Extracted (HPLC) | Activity (Quick Test) |
|---|---|---|---|
| PVPP | pH 8.5 displacement of solubilized complex | Good | Very Poor |
| XAD-2 Resin | pH 8.5 displacement of solubilized complex | None | — |
| Ultrafiltration | MW 10,000 membrane | Good | Very Poor |
| | MW 2,000 membrane | None | — |
| Preparative HPLC | 85% aqueous acetone eluent | Moderate | Very Poor |

C. Enzymatic Treatment

Seven different proteolytic enzymes are reacted with isolated acid-precipitated complex. The enzymes are: protease from Aspergillus sojae, protease from papaya, protease from Streptomyces griseus, protease from Subtilopeptidase A, pronase, papain, and pepsin.

In each experiment, 10 mg of enzyme is dissolved in 20 ml of phosphate buffer at a pH near that recommended by the manufacturer and added to non-dried complex (1 gram). For those enzymes that are dissolved in acid media, the complex remained insoluble during an eight-hour incubation at the temperature recommended by the manufacturer for optimum activity. The solutions are checked for solubilized gallotannin and the activity checked by the quick test. For those enzymes that are dissolved in basic media, the complex also dissolved and the reaction is carried out in complete solution for eight hours at the temperature recommended by the manufacturer for optimum activity. Each reaction mixture is then analyzed for gallotannin and activity by the quick test.

TABLE NO. 4

ENZYMATIC REACTION WITH SCHOENE SLUDGE

| Type | Special Conditions | Gallotannin Extracted (HPLC) | Activity (Quick Test) |
|---|---|---|---|
| Protease (Asp. sojae) | pH 8.5, 37° C. of solubilized complex | None | — |
| Protease (papaya) | pH 7.5, 37° C. of solid complex | None | — |
| Protease (Strep. griseus) | pH 8.5, 30° C. of solubilized complex | None | — |
| Protease (Subtilopeptidase A) | pH 8.5, 37° C. of solubilized complex | None | — |
| Pronase | pH 7.5, 37° C. of solid complex | None | — |
| Papain | pH 4.6, 25° C. of solid complex | None | — |
| Pepsin | pH 2.0, 37° C. of solid complex | None | — |

D. Ketone Extractions

1. Methyl Isobutyl Ketone

Two hundred ml of methyl isobutyl ketone is mixed with 50 ml of water and the two phase mixture is added to approximately 100 ml of undried acid-precipitated complex. The mixture is stirred for eight hours. The solvent is decanted and the organic layer is separated from the water layer using a separatory funnel. Both solutions are examined for extracted gallotannin by HPLC and activity by the quick test.

2. Acetone a. In four separate experiments, approximately 100 ml of undried complex is extracted two times each with 200 ml of a mixture of 50% acetone/50% water; 70% acetone/30% water; 85% acetone/15% water; and 90% acetone/10% water for four hours at room temperature. Each extract is decanted off the solid material and air-dried in a hood. The dried extracts are reextraced with methanol and tested for gallotannin and activity by the quick test.

b. Schoene sludge is air-dried to give granular material of approximately 2% weight percent moisture. This material (381 grams) is extracted with 800 ml of 90% acetone/10% water with occasional manual stirring for four hours. After settling a short time, the clear solvent is decanted off to give 500 ml of extract and a tacky residue. The residue is reextracted with 800 ml of 90% acetone for another four hours and the decant poured into a separate beaker (700 ml). A third extraction is made with 90% acetone overnight at room temperature. This yields 790 ml of extract. The three solutions are individually air-dried.

TABLE NO. 5
EXTRACTION OF SCHOENE SLUDGE WITH KETONES

| Ketones | % $H_2O$ | Gallotannin Extracted(HPLC) | Activity (Quick Test) |
|---|---|---|---|
| Methyl Isobutyl Ketone (MIBK) | 20% as two-phase | Moderate | Moderate |
| Acetone | 50 | Moderate | Poor |
| Acetone | 30 | Moderate | Poor |
| Acetone | 15 | Good | Good |
| Acetone | 10 | Very Good | Very Good |

The figure shows a chromatographic conparison of the recovered active gallotannin from schoene sludge with a commercial tannin and the recovered material is substantially identical to the commercial product.

The recovered gallotannins also can be converted to propyl gallate which is a food antioxidant in wide use in the United States.

This invention is intended to cover all changes and modifications of the example of the invention herein chosen for purposes of the disclosure which do not constitute departures from the spirit and scope of the invention.

What is claimed is:

1. A process for recovering active gallotannins from schoene sludge comprising the steps of
   (a) recovering schoene sludge from beer, and
   (b) extracting the sludge with a mixture of acetone and water such that the ratio of acetone to water in the sludge during treatment is about 85:15 to about 95:5.

2. The process of claim 1 wherein the ratio of acetone to water is about 88:12.

3. The process of claim 1 including the step of drying the schoene sludge to less than about 5% water before extracting the acetone-water mix.

4. The process of claim 3 wherein the sludge is extracted with about 3 liters of about 88% acetone-water mix per kg of dried sludge.

5. The process of claim 1 wherein the sludge is extracted at least two times with the acetone-water mix and the solvent is recycled.

6. The process of claim 1 including the additional steps of treating the residue from the acetone-water extraction with a mixture of ethyl acetate and water and recovering gallotannin.

7. The process of claim 1 including the additional steps of dissolving the residue from the acetone-water extraction in water, filtering, treating the aqueous extract with an equal volume of ethyl acetate, separating the ethyl acetate and recovering a dry purified gallotannin product.

8. A process of claim 6 including the additional steps of drying the gallotannin, dissolving it in water, and spray drying to produce a purified reusable gallotannin powder.

9. A process for recovering active gallotannins from schoene sludge comprising the steps of
   (a) extracting schoene sludge recovered from beer with a mixture of acetone and water at a temperature of at least about 60° C. such that the ratio of acetone to water in the sludge is about 85:15 to about 95:5,
   (b) separating the acetone,
   (c) dissolving the residue in water,
   (d) extracting the residue with ethyl acetate and water,
   (e) separating the ethyl acetate, and
   (f) recovering active gallotannins.

10. The process of claim 9 including the additional steps of dissolving the active gallotannins in water, spray drying and recovering a purified reusable gallotannin powder.

11. The process of claim 9 including the step of drying the schoene sludge to below about 5% moisture before treating with the acetone-water mix.

12. The process of claim 9 wherein the ratio of acetone to water in the sludge during extraction is approximately 88:12.

13. The process of claim 9 wherein the residue from the acetone-water extraction is filtered after being dissolved in water and the filtrate is treated with about an equal volume of ethyl acetate.

14. The process of claim 9 wherein the acetone-water extraction is repeated, the extracts are combined, and the acetone is recycled.

15. The process of claim 9 wherein the ethyl acetate-water extraction is repeated, the extracts are combined, and the ethyl acetate is recycled.

16. A process for recovering active gallotannins from schoene sludge comprising the steps of
   (a) treating schoene sludge recovered from beer with a mixture of acetone/water from about 50:50 to about 70:30 (v/v) to precipitate out yeast solids,
   (b) treating at least the liquid part of the material of step (a) with 100% acetone to produce a mixture of acetone/water of about 85:15 to about 95:5 (v/v) to precipitate out the complexed protein and solubilize the active gallotannins, and
   (c) recovering the active gallotannins.

17. The process of claim 16 wherein the sludge is treated at room temperature with agitation in step (a).

18. The process of claim 16 wherein the yeast solids are separated from the supernatant before the supernatant is treated with the acetone/water mixture of step (b).

19. The process of claim 16 wherein substantially pure acetone is added to the liquid in step (b) to produce the desired acetone/water mix.

20. The process of claim 18 wherein substantially pure acetone is added to supernatant to produce the desired acetone/water ratio.

21. The process of claim 16 wherein the acetone/water mixture in step (b) is about 88:12.

22. The process of claim 16 wherein the recovery of gallotannins in step (c) also includes the steps of recovering the acetone, adding water to the residue to remove remaining water insolubles, extracting the aqueous solution with ethyl acetate, recovering the ethyl acetate, and spray drying the remainder to give active tannin in powder form.

* * * * *